United States Patent [19]

Saab

[11] Patent Number: 5,411,477
[45] Date of Patent: May 2, 1995

[54] HIGH-STRENGTH, THIN-WALLED SINGLE PIECE CATHETERS

[76] Inventor: Mark A. Saab, 396 Andover St., Lowell, Mass. 01852

[21] Appl. No.: 59,725

[22] Filed: May 10, 1993

Related U.S. Application Data

[63] Continuation of Ser. No. 522,178, May 11, 1990, abandoned.

[51] Int. Cl.⁶ .............................................. A61M 29/00
[52] U.S. Cl. .................................... 604/96; 606/192; 606/194; 264/521; 425/526
[58] Field of Search ................ 604/96; 606/192, 194; 264/520–524, 528, 529, 535; 425/526

[56] References Cited

U.S. PATENT DOCUMENTS

| | | | |
|---|---|---|---|
| Re. 32,983 | 7/1989 | DuPont . | |
| Re. 33,561 | 3/1991 | Levy .................................. | 604/96 |
| 2,568,128 | 9/1951 | Morris ................................ | 264/523 |
| 3,271,484 | 9/1966 | Brillinger ........................... | 425/526 |
| 3,733,309 | 5/1973 | Wyeth et al. . | |
| 4,254,774 | 3/1981 | Boretos . | |
| 4,317,793 | 3/1982 | Hubert et al. ...................... | 264/521 |
| 4,339,409 | 7/1982 | Curto ................................. | 264/521 |
| 4,411,055 | 10/1983 | Simpson et al. . | |
| 4,467,790 | 8/1984 | Schiff ................................. | 604/96 |
| 4,490,421 | 12/1984 | Levy . | |
| 4,512,948 | 4/1985 | Jabarin ............................... | 264/521 |
| 4,701,121 | 10/1987 | Jakobsen et al. ................... | 425/526 |
| 4,820,349 | 4/1989 | Saab . | |
| 4,871,507 | 10/1989 | Ajmera .............................. | 264/521 |
| 4,938,676 | 7/1990 | Jackowski et al. ................. | 264/530 |
| 4,941,877 | 7/1990 | Montano, Jr. ..................... | 604/96 |
| 4,950,239 | 8/1990 | Gahara et al. ..................... | 604/96 |
| 4,952,357 | 8/1990 | Euteneuer ......................... | 604/96 |
| 5,149,485 | 9/1992 | Belcher ............................. | 425/526 |
| 5,270,086 | 12/1993 | Hamlin ............................. | 604/96 |

FOREIGN PATENT DOCUMENTS 0274411 7/1988 European Pat. Off. .

OTHER PUBLICATIONS

Levy, Stanley B., "Improved Dilatation Catheter Balloons", *Journal of Clinical Engineering*, vol. 11, No. 4, Jul.–Aug., 1986, pp. 291–296.

*Primary Examiner*—C. Fred Rosenbaum
*Assistant Examiner*—Ronald K. Stright, Jr.
*Attorney, Agent, or Firm*—Lappin & Kusmer

[57] ABSTRACT

An integral, single-piece, high-strength, thin-walled, inflatable catheter is disclosed. The catheter has one end partially or entirely closed, and is at least uniaxially oriented along its entire length. The method and apparatus for making the catheter is also disclosed. The catheters of this invention have a calculated radial tensile strength of about 10,000 psi or greater at every point along the catheter.

28 Claims, 4 Drawing Sheets

HIGH-STRENGTH, THIN-WALLED SINGLE PIECE CATHETERS

This is a continuation of application Ser. No. 07/522,178, filed on May 11, 1990, now abandoned.

BACKGROUND OF THE INVENTION

The present invention relates broadly to high-strength, thin-walled catheters, and more specifically to single-piece, extremely thin-walled, inflatable catheters formed with an oriented polymer having an extremely high tensile strength.

Many diagnostic and/or therapeutic catheters and other medical instruments are often provided near their distal ends with inflatable thin-walled balloons for dilating a particular body part once such device is properly positioned in the body. The balloon is usually separately formed as a sleeve or segment having an enlarged middle section and a reduced diameter at its opposite open ends. The ends are formed so that they can be secured around the periphery of the shaft of the catheter body so as to form a sealed balloon structure. Typically, the balloons collapse about the shaft of the catheter extending through the balloon portion so that the catheter can be directly intubated, or moved through a guide tube previously intubated, in the body. Usually, the balloon portion of the catheter is moved beyond the guide with the balloon portion at the site of interest. Balloon segments are made as thin as possible so that it provides minimal contribution to the overall outer diameter of the catheter when the balloon is deflated. This minimizes the internal as well as the external diameter of the guide tube. Typically, the guide tube must be sufficiently stiff, yet flexible, so that it can be intubated along what sometimes are tortuous paths within the body. See, for example, my U.S. Pat. No. 4,820,349 directed to "Dilatation Catheter With Collapsible Outer Diameter" and issued Apr. 11, 1989. One common application of thin-walled balloon catheters is in the balloon angioplasty procedure wherein the balloon segment at the distal end of the catheter is inflated inside a partially blocked artery section in order to reduce the blockage. Balloon catheters also have applications in other medical procedures involving insertion into blood vessels and other body cavities. Such applications for thin-walled balloon catheters are well-known in the art.

Of critical importance in all such internal applications for thin-walled balloon catheters is that the balloon must be secured to the shaft of the catheter and be of a sufficiently high-strength so as to be resistant to rupture. During use the balloon is filled with a fluid (liquid or gas) usually through the body of the catheter, and a rupture would lead to leakage of a foreign substance into the blood vessel or other body part with potentially harmful results. In addition, it might then be difficult or impossible to withdraw the catheter without trauma to the surrounding tissue. The danger of rupture is particularly great in connection with balloon catheters inflated with a fluid under elevated pressure. In the case of the balloon angioplasty procedure, where the internal diameter of the catheter is relatively small, not only must the pressure be relatively high to inflate the balloon inside a partially blocked artery section but, in addition, the procedure typically involves several inflation-deflation cycles thereby putting further strain on the catheter.

In response to these special demands, materials and procedures have been developed for making high-strength, thin-walled catheter balloon segments for such applications. For example, U.S. Pat. No. Re. 32,983, reissued Jul. 11, 1989, (originally U.S. Pat. No. 4,490,421 to Levy) describes a polymeric balloon having a burst pressure of at least 200 psi. The Levy patent discloses a process for biaxial orientation of polymeric tubing under certain temperature conditions in order to achieve an improved, high-strength dilatation balloon segment. The biaxial orientation of orientable polymers has been found to create very thin films having extremely high tensile strength, far beyond any properties achievable with prior art processes and materials. Levy's preferred polymer is polyethylene terephthalate (PET) having the desirable trait of being relatively non-compliant at body temperature when the material has been highly biaxially oriented.

In accordance with Levy's process, a balloon segment can be produced by extending a length of PET tubing of appropriate dimensions through a mold and out an opening provided at the bottom of the mold. The open end of the tube extending out the bottom of the mold is pinched or clamped off. The portion of the tube within the mold is then heated to a suitable temperature and drawn (stretched) longitudinally to a length 3–6 times its original length by allowing weights or a mechanical stretching device to pull the closed end of the tube. The portion of the drawn tubing inside the mold is then radially expanded at an elevated temperature by introducing a pressurized fluid into the tube. A further description of the Levy dilatation balloons and process appears in the Journal of Clinical Engineering, vol. 11 (July–August 1986), pp. 291–296. One principal advantage of using PET to make the balloon segment is that the material can be stretched very thin, yet because of the biaxial orientation of the polymer it has an extremely high tensile strength and is capable of withstanding high pressures. Recognition of the special high-strength properties of biaxially oriented cylindrical PET objects dates back to at least 1973 when U.S. Pat. No. 3,733,309 was issued to Wyeth et al. directed to high-strength plastic bottles produced using a biaxial orientation process.

More recently I have been issued U.S. Pat. No. 4,820,349 directed to "Dilatation Catheter With Collapsible Outer Diameter," and mentioned above. In the preferred embodiment described in this patent, the balloon segment is made from PET. In a related application, filed in my name and published Jul. 13, 1988 by the European Patent Office as Printed Specification No. 0274411 under the title "Thin Wall High Strength Balloon and Method of Manufacture," I describe the use of thin wall tubings combined with high-stretch ratios and heat setting to provide balloon segments having thin, strong and flexible properties. All of the aforementioned patents and related literature are incorporated herein by reference.

A remaining problem with the balloon segments and associated catheters made in accordance with the prior art, including my previously described inventions, is the adhesive joints at which the balloon segment is attached to the inner shaft. First, it is relatively costly, cumbersome and time-consuming to effect the adhesive seals. Each seal must be complete and perfect in order to avoid leakage of the pressurizing fluid used to inflate the balloon. The adhesive joints represent points of discontinuity and weakness along the outer skin of the catheter. The flexibility of the portion of the catheter provided with the adhesive is reduced due to the relative stiffness of the cured adhesive. The adhesive must meet demanding performance specifications including adhesion to both the high-strength polymeric balloon segment material as well as to the inner shaft extending through the balloon segment. The adhesive must be non-toxic, non-allergenic, and not susceptible to deterioration or chemical attack under conditions of use. Welding or heat sealing pre-formed catheter balloon segments to another catheter element are alternative approaches that do not require adhesives but are also difficult and relatively expensive. Such procedures also invariably lead to partial loss of biaxial orientation of the balloon segment at the fusion points producing weaknesses in the final product. For all of these reasons, it would be highly desirable to provide thin-walled balloon catheters that are free of any adhesive or welded joints.

U.S. Pat. No. 4,254,774 to Boretos specifically recognizes the desirability of forming a balloon catheter such that "the balloon is a continuous, non-interrupted integral part of the catheter wall, free of seams or joints," (col. 1, lines 7-9). Boretos addresses this problem by applying internal fluid pressure to heated plastic tubing in order to create a balloon at one end thereof. Only the balloon portion of the tubing is stretched. The remaining part of the tubing, i.e. the catheter shaft, remains thick and relatively low strength, especially if made with any one of the specific materials identified by Boretos. The balloon is adapted to be invaginated into the shaft of the catheter prior to inserting the catheter into the body passageway of interest. In one embodiment, Boretos uses a mold to better shape the balloon portion of his catheter. The Boretos process, however, involves the manufacture of extremely small catheters having diameters of 5 to 40 mils with relatively thick walls of 2 mils to produce balloons of 100 mil diameters for traversing vessels of 1 mm. (0.03937 inches or 39.37 mils). The balloon portion of the catheter is relatively elastic because the catheter is utilized for partial or total occlusion of a passageway and may be used to deliver substances to a particular site through a performed hole in the inflated balloon. The catheter body or shaft remains relatively thick for its diameter so as to maintain sufficient stiffness so that it can be intubated within a body passageway, and yet sufficiently flexible so that it can follow a tortuous path through the body. While the balloon portion of the Boretos catheter is stretched there is no recognition in Boretos of the special advantages of biaxial orientation of orientable polymers under specific conditions, and no means is suggested by Boretos for carrying out a biaxial orientation of the entire body of the catheter. It is well known that tubing of virtually all unoriented or unreinforced thermoplastic materials has a radial tensile strength of less than 10,000 psi, most being less than 5,000 psi.

U.S. Pat. No. 4,411,055 to Simpson et al. also discloses an embodiment for a dilating catheter assembly "in which an inflatable or distensible balloon-like portion is formed integral with one of the tubular members forming the dilating catheter assembly," (col. 2, 11. 15-18; also, col. 10, lines 32-38). Although the disclosure in Simpson is incomplete with regard to their description of such an embodiment, it is clear that Simpson et al., as in the case of the Boretos patent, do not recognize or discuss the special advantages of using biaxially oriented polymers, nor is any means suggested for carrying out a uniaxial or biaxial orientation of the resulting integral structure.

Finally, guide catheters for receiving and guiding diagnostic and/or therapeutic catheters, must be sufficiently stiff so that it can be inserted into and moved through a particular part of the body, yet sufficiently flexible so that it can follow tortuous paths through the body. With the increased use of laser and ultrasound delivered through a diagnostic and therapeutic catheter, such as suggested in U.S. Pat. No. 4,821,731 (Martinelli), it is desirable to manufacture a guide catheter having a wall sufficiently thin and made of a suitable material transmissive to ultrasound and infrared laser radiation produced, for example, by a YAG laser frequently used for surgical procedures. While PET is a suitable material, it must be at most 1.5 mils thick.

OBJECTS AND SUMMARY OF THE INVENTION

Accordingly, it is a principal object of the present invention to provide an integral, single-piece, seamless, high strength, thin-walled, inflatable catheter.

It is also an object of this invention to provide an integral, single-piece, seamless, high-strength, inflatable, thin-walled catheter comprising a self-supporting, orientable polymer tubing that has been oriented throughout the tubing at least uniaxially.

A further object of this invention is to provide an integral, single-piece, thin-walled, seamless catheter comprising a tubular body having a distal end which is substantially closed and made of a material which is at least uniaxially oriented over the entire length of the catheter.

Still another object of this invention is to provide a self-supporting, thin-walled catheter that has a calculated radial tensile strength of about 10,000 psi or greater at every point along its length.

These and other objects and advantages are achieved by a unitary, integral and seamless catheter comprising orientable polymeric tubing having a substantially closed end and made from a material that has been oriented at least uniaxially along its entire length so as to provide an extremely thin-walled, self-supporting, inflatable catheter.

Other objects of the invention will in part be obvious and will in part appear hereinafter. The invention accordingly comprises the processes involving the several steps and the relation and order of one or more of such steps with respect to each of the others, and the products and compositions possessing the features, properties and relation of elements exemplified in the following detailed disclosure and the scope of the application all of which will be indicated in the claims.

BRIEF DESCRIPTION OF THE DRAWINGS

For a fuller understanding of the nature and objects of the present invention, reference should be had to the following detailed description taken in connection with the accompanying drawings wherein.

DETAILED DESCRIPTION OF THE INVENTION

In accordance with the present invention the inflatable catheter is made as an integral piece with a substantially closed end. The material forming the wall of the one piece catheter must be as thin as possible so that it easily can be used for various applications, including use as a guiding catheter for receiving and guiding a diagnostic and/or therapeutic catheter or other medical instruments without significantly increasing the overall diameter of the latter devices during use within the body. Additionally, the wall of the catheter should be thin enough and made of a suitable material which is substantially transmissive to both ultrasound and infrared laser radiation typically generated from the distal section of certain diagnostic and/or therapeutic catheters so that the catheter will not interfere with the use of the ultrasound and laser devices. The material must also be strong, i.e. having a radial tensile strength of about 10,000 psi or greater, to withstand relatively high pressures, up to 200 psi and higher, although the materials can be designed to provide a lower burst pressure for certain applications. As described above, PET has proven to be very strong and useful as balloon segments for balloon catheters, when the material is biaxially oriented. It has been found that this material also has excellent properties for transmitting ultrasound and infrared laser radiation produced, for example, by a YAG laser of a type typically used for medical applications if made sufficiently thin, i.e., less than 1.5 mils. However, it is desirable to make the wall thickness of much smaller dimensions, since a smaller thickness can yield a particular inner diameter dimension of the catheter with a smaller outer diameter, or a particular outer diameter dimension with a larger inner diameter. In addition, decreasing the wall thickness increases the flexibility since the stiffness of a material is related to the cube of the thickness dimension so that, for example, reducing the thickness by one-half reduces the stiffness by a factor of 8. This can be advantageous in at least some applications since the increased flexibility makes the entire catheter inflatable. Accordingly, PET is the preferred material, although other orientable polymers suitable for biaxial orientation can also be used, such as nylon, since the orientation of such materials decreases the wall thickness while increasing the tensile strength of such materials. Accordingly, oriented polymers as thin as 0.0005 inches or smaller can be used, depending on the final diameter(s) of the finished catheter design as will be more apparent hereinafter.

Figure 1:
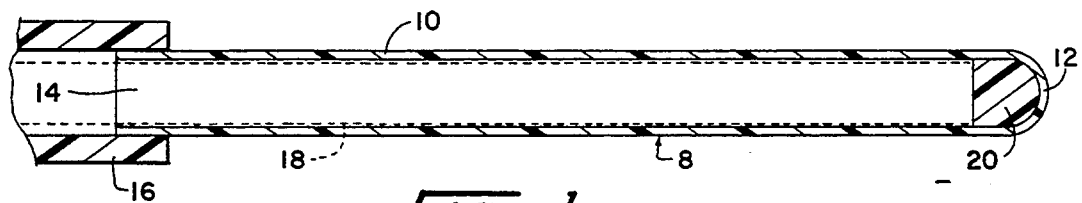
FIG. 1 is a cross-sectional, radial view taken along the longitudinal axis of a single-piece, constant diameter, thin-walled, inflatable catheter designed and made in accordance with the present invention.

FIG. 1 shows a cross-sectional view of a single-piece, thin-walled, high-strength, inflatable catheter 8 made in accordance with the present invention. The catheter 8 is particularly useful for lumens of the body which are fairly straight with little bending, such as the esophagus, urethra tract, etc. Catheter 8 comprises the main body 10 and tip 12 at the distal end of the catheter. The tip is a "substantially closed end" which term includes a closed sealed end (which is preferred) or a tip formed with a small hole. FIG. 1 represents a single-piece inflatable catheter without a balloon portion (i.e. it is a "constant diameter" catheter). The single-piece catheters of this invention may be made of any length, ranging, for example, from as little as about 10 centimeters to two meters or more, depending on the application.

The width, or outside diameter, of the finished constant diameter catheter may also vary, for example from as small as 1 mm or less to as large as 25 mm or more. The thickness of the wall of the catheters of this invention will be a function of the diameter, as will be described in greater detail hereafter. Although the material used is relatively inelastic at body temperature, it is sufficiently flexible (thin-walled) so that it can be inflated and deflated by introducing and withdrawing fluid from the open proximal end 14 of the catheter. Yet the stiffness of the resulting catheter wall will be insufficient to insert and move the catheter in its deflated state through a lumen in the body. Nevertheless, because the catheter is constructed as a single piece without permanently securing it at two axial positions to a shaft running through the center of catheter (as in the case of the balloon segments of the balloon catheters of the prior art discussed above) the catheter is considered to be and is herein referred to as "self-supporting".

The open proximal end 14 of the catheter 8 can be provided with a suitable fitting 16 so that a suitable stiffening member, indicated in phantom at 18, can be inserted into the catheter for making the catheter sufficiently stiff so that it can be inserted into and navigated through the lumen of the body. Once the catheter is in position, the stiffening member can be removed. Alternatively, a source of pressurized fluid can be connected to fitting 16 and fluid introduced through the end 14 into the interior of the catheter so that the catheter becomes relatively stiff and pushable through a body lumen. In order to assist the alignment of the stiffening member 18 and catheter 8, the tip 12 of the catheter can be provided with a plug 20 made of a suitable material such as an elastomeric material, such as a silicone, or a rigid material such as epoxy, for aiding the insertion and navigation of the catheter through a lumen of the body, and configured to receive the end of the stiffening member. Alternatively, the tip can be formed as a hollow closed end tip for receiving the similarly shaped end of the stiffening member, the tip having a smaller inner dimension (e.g., diameter) than the inner diameter of the remaining portion of the main body 10 of the catheter. It should be appreciated that stiffening member 18 may be a diagnostic and/or therapeutic catheter or other medical instrument constructed to be used with catheter 8.

Figure 2:
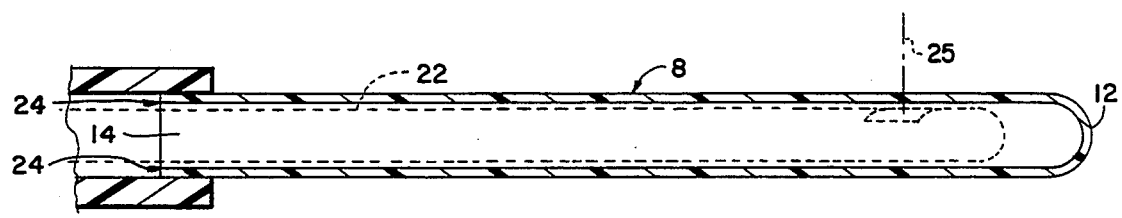
FIG. 2 shows the catheter of FIG. 1 used as a guide catheter for receiving a diagnostic and/or therapeutic catheter or other medical instrument.

It should be noted that the external surface of the main body 10 is completely smooth and continuous with no joints, seams or discontinuities, although specific geometric features, such as a marker ring, can be formed on the body 10, if desired. A catheter 8 such as shown in FIG. 1 may be intubated and used to house and guide a diagnostic and/or therapeutic catheter or other medical instrument indicated in phantom at 22 in FIG. 2, through an internal body lumen. In the latter case if the stiffening member 18 initially used to position the catheter 8, can be removed and the diagnostic and/or therapeutic catheter 22 is inserted into the catheter 8 through and secured with fitting 16 as shown in FIG. 2. Once secured, the fitting may allow introduction of a fluid indicated by arrows 24, into the proximal open end 14 so as to inflate the catheter 8. Ultrasound and laser beams then can be generated from the catheter 22 as shown by ultrasound and radiation projection axis 25.

Figure 3:
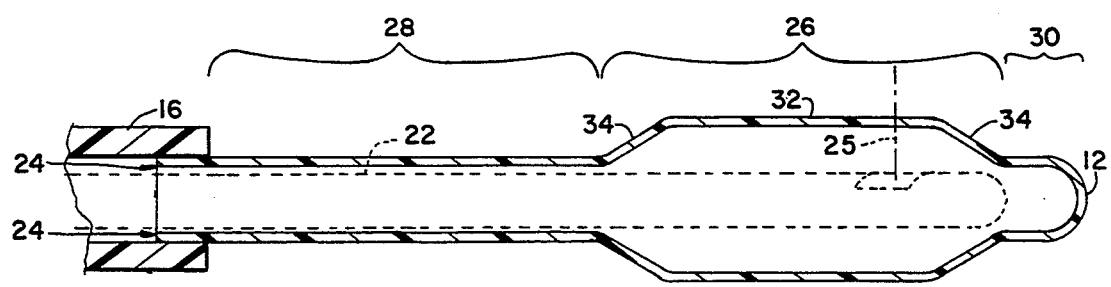
FIG. 3 is a cross-sectional radial view taken along the longitudinal axis of a single-piece, thin-walled, inflatable catheter designed and made according to the present invention having a body portion and a balloon portion and showing the balloon portion in the inflated state.
Figure 4:
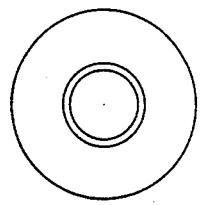
FIG. 4 shows an end view of the catheter of FIG. 3 in the inflated state.
Figure 5:
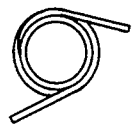
FIG. 5 shows an end view of the catheter of FIG. 3 in the deflated state.
Figure 6:
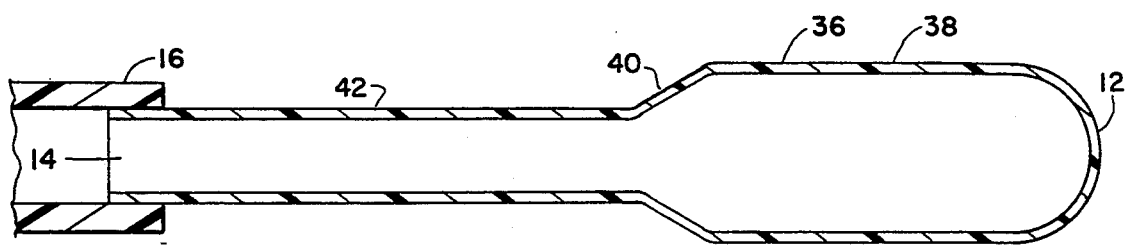
FIG. 6 is a cross-sectional radial view along the longitudinal axis of yet another balloon catheter designed and made in accordance with the present invention.

Referring to FIGS. 3–5, the self supporting, single piece, thin-walled catheter can also be formed with a balloon portion 26 disposed between the proximal body portion 28 and distal body portion 30. The balloon portion 26 includes an enlarged diameter middle section 32 which tapers down at both ends at frusto-conical or transition sections 34 to the respective body portions 28 and 30, the latter being of the same constant diameter (although the diameters of portions 28 and 30 can be different or vary along the longitudinal axis of the catheter). Alternatively, the balloon portion 36 can be formed in the distal end of the catheter as shown in FIG. 6, wherein the balloon includes an enlarged diameter section 38 and a frusto-conical or transition section 40. Section 40 joins section 38 to the smaller, constant diameter proximal body portion 42.

Figure 7:
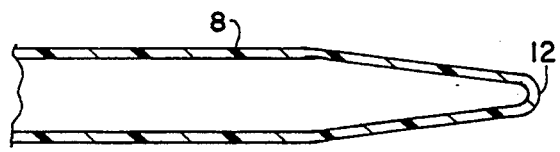
FIG. 7 is a cross-sectional radial view, partially cut away, along the longitudinal axis of a modification of the closed end tip of a catheter designed and made in accordance with the present invention.
Figure 8:
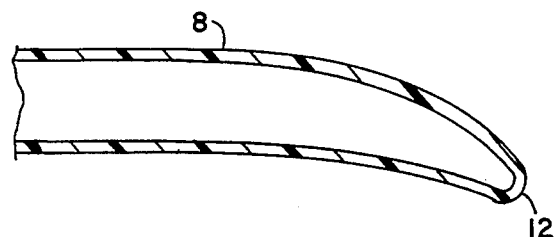
FIG. 8 is a cross-sectional radial view, partially cut away, along the longitudinal axis of another modification of the closed end tip of a catheter designed and made in accordance with the present invention.

The entire catheter including the balloon portions 26 and 36 of the catheters in FIGS. 2–5 will be relatively flexible and collapsible when they are deflated as illustrated in FIGS. 4 and 5, wherein FIG. 4 shows the inflated state, while FIG. 5 shows the balloon portion collapsed about a stiffening member or the diagnostic and/or therapeutic catheter such as member 12 or catheter 22 shown in FIGS. 1, 2 and 3. But, when the catheter of FIG. 3 or 6 is inflated with a pressurized fluid, balloon portions 26 and 36 each inflate to a rigid lumen having an external diameter D larger than the width of the small diameter body portions 28, 30 (FIGS. 3–5) and 42 (FIG. 6). The tip 12 of each of the catheters described is shown as a rounded end so as to form a sealed end closure so that the fluid can not leak from the end. It should be appreciated that in some applications the tip may be formed with other geometric configurations such as a tapered tip as shown in FIG. 7, and a curved tip (tapered or untapered) as shown in FIG. 8. In addition, as described hereinafter, small holes can be formed in the tip. Such holes can be useful in providing irrigating fluids and the like to the body site where the distal end of the catheter is positioned, or purging the catheter of air, or other fluid, when filling it with another fluid.

The single-piece, self supporting catheters of this invention are formed to be very thin-walled, highly flexible and strong enough to withstand dilatation pressures. This is accomplished by at least uniaxially orienting, and preferably biaxially orienting a tubular member comprising an orientable polymer under certain temperature conditions. The polymeric materials suitable for biaxial orientation and the temperature conditions for the expansion and subsequent heat setting step are well-known in the art as discussed in the prior art cited above. In the preferred embodiment of this invention, the catheters are formed from PET tubing of appropriate starting dimensions relative to the desired final catheter shape, size, and strength characteristics, as will be described hereinafter.

Figure 9:
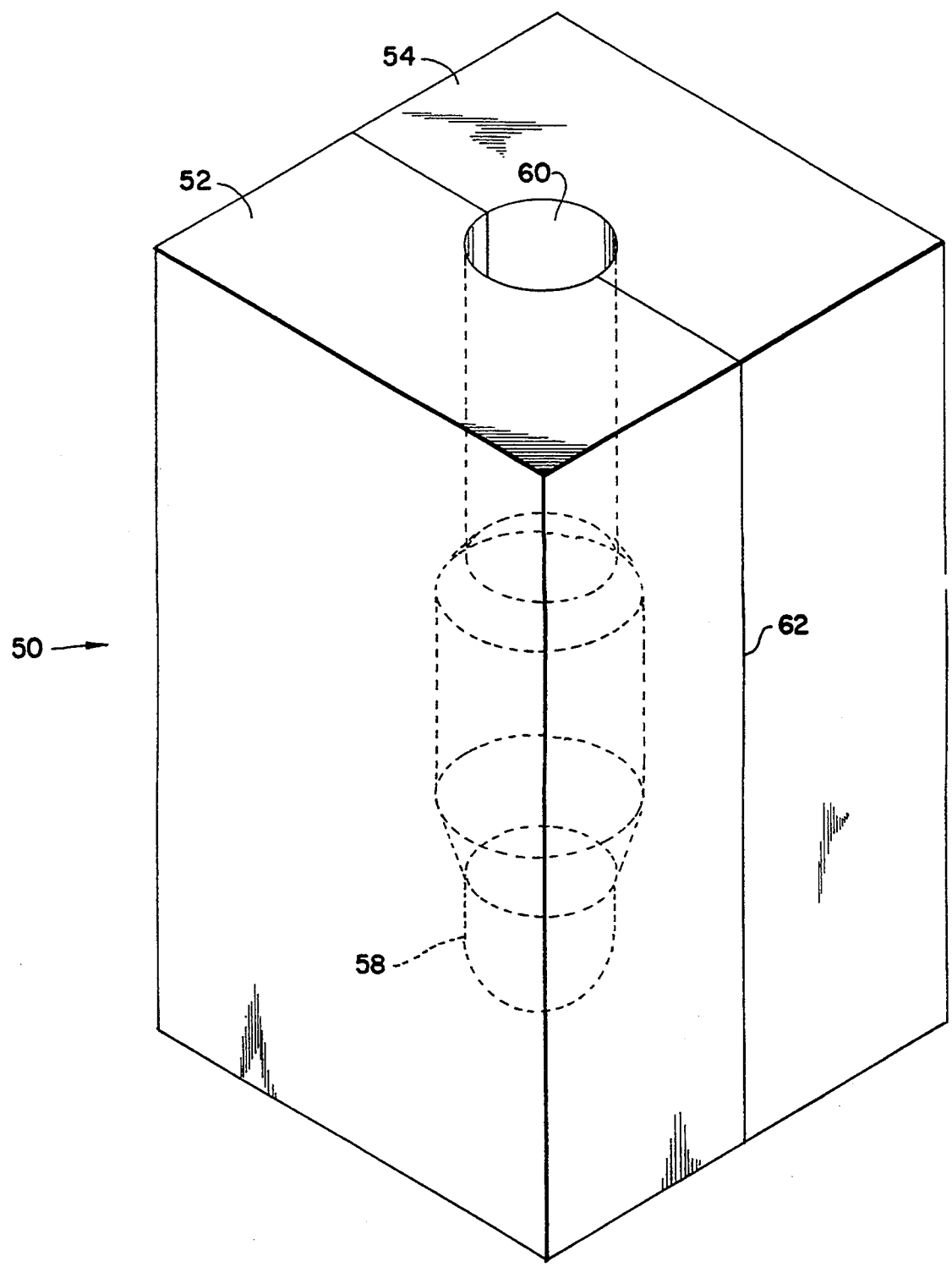
FIG. 9 is a schematic, isometric view of a two-piece mold for forming the single-piece catheters of the present invention.

FIG. 9 is a schematic view of a mold 50 that can be used to form the single-piece catheters of the present invention. The mold as shown comprises a body portion consisting of two half sections 52 and 54. Means are provided for securely mating the respective half sections in alignment in order to define an internal chamber or cavity 58 having a configuration that is the desired final shape of the catheter when inflated with an opening 60 from the top of the mold into the cavity.

One means for securing the half sections of the mold comprises hinge means 62 positioned respectively along one side of the body half sections along the juncture line with clasp means (not shown) on the opposite side along the opposite juncture line. Other conventional means for aligning, securing and detaching the mold half sections are intended to be encompassed by this invention. Although a mold in half sections as discussed herein is advantageous in permitting ready access to the mold interior, other mold constructions such as sleeve or tube molds can also be used and are intended to be encompassed by this invention.

The cavity of the mold as shown in FIG. 9 is configured so that it will form single-piece balloon catheters of the shape illustrated in FIGS. 3–5. When fully inflated in use, the catheter would have the same size and shape as internal chamber 58. To form a single-piece catheter without a balloon portion, as illustrated in FIG. 1, internal chamber 58 would be cylindrical in shape having a constant cross-sectional diameter for the entire longitudinal length of the cavity.

The major parts of the mold are made from a material, such as brass, having good heat conductivity. Means are also provided for heating the interior cavity 58 of the mold. Any conventional means (not shown) for heating and regulating the temperature of the mold, such as electrical resistance heating with thermostatic controls, fluid jackets to contain circulating fluids at elevated temperatures, etc., may be used with this invention. Of course, the mold must be adapted to accommodate the heating and temperature control systems.

It is envisioned as a part of this invention that the mold may have a plurality of heating zones separated by heat insulators and independently regulated in order to achieve single-piece catheters having special properties. For example, it may be desirable to maintain a temperature gradient or differential in internal chamber 58 during the expansion step and/or during the subsequent heat setting step. Such a temperature gradient or differential during the expansion or heat setting steps could be used, for example, to achieve a higher degree of molecular orientation (meaning greater strength and greater flexibility) in the balloon portion of the catheter while retaining a lower degree of molecular orientation (and therefore greater rigidity due to its greater thickness) in the distal or proximal body portions of the finished catheter. Temperature gradients and differentials during the biaxial orientation steps can also be used to achieve varying wall thicknesses and tensile strengths along the length of the final catheter. Such variations and special properties are within the ambit of routine experimentation, and are intended to be encompassed by this invention. It should also be appreciated that the greater the degree of orientation of polymer the higher the tensile strength of the material and the more inelastic the material will be. Thus, a greater degree of orientation can be provided to select portions of the catheter providing greater strength but relatively greater inelasticity that other portions of the catheter, with the latter portions being relatively more elastic. Nevertheless, the degree of orientation for all of the catheters should be sufficient to provide a minimum radial tensile strength of about 10,000 psi, regardless of any variations in orientation that might be desirable.

In addition, although the mold process and apparatus described herein is preferred for large volume production, it is envisioned that the single-piece catheters of this invention could be formed in other ways using a controlled temperature environment and appropriate tools or machinery for biaxial orientation of the polymeric tubular members. This invention is intended to cover biaxially-oriented, single-piece self supporting catheters made by any such techniques.

Figure 10B:
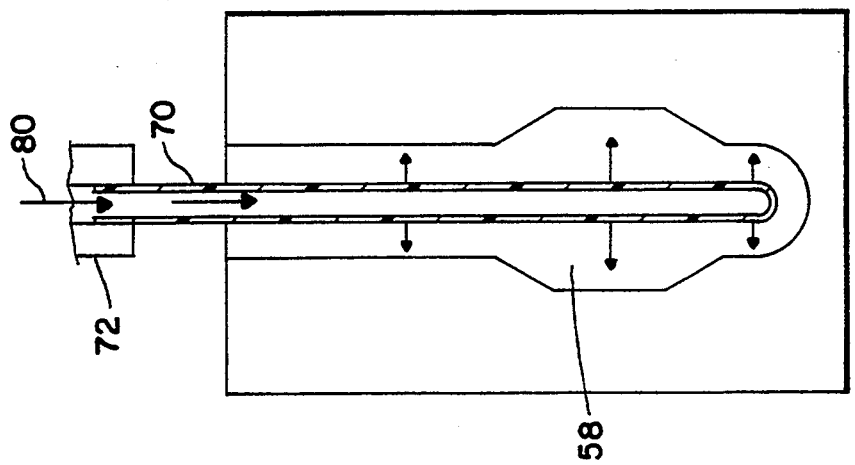
FIGS. 10A and 10B are cross-sectional views of the interior of the mold along the interface of the two-pieces of the mold shown in FIG. 9, and illustrating the preferred embodiment of the method of the present invention.
Figure 10A:
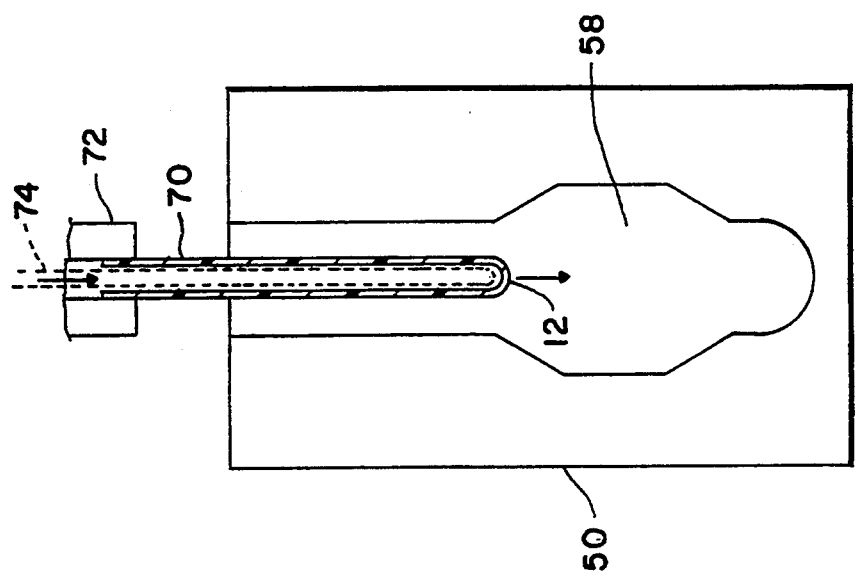

Referring to FIGS. 10A and 10B, the process of making a one-piece catheter in the mold of FIG. 9 will now be described. Tubing 70 of polymeric material is formed with a predetermined initial outer diameter, thickness and length by, for example, extruding the tubing in a manner well known in the art. The tubing is initially processed to form a closed end by any well known technique, such as thermal sealing the end of the polymeric tubing with heat or ultrasound, or insert or overmolding the end of the tubing so as to mold a hemisphere on the end of the tubing. As is well known, the sealed end should be initially amorphous so that preferably it can be subsequently substantially oriented when it is stretched. FIG. 10A shows a clamp 72 for holding the proximal end of the tubing 70 during the expansion process. Also shown is a cross-sectional view of a narrow, rigid tube or rod 74 used for axially expanding the tubing 70. Rod 74 has a proximal end and a distal end, the latter being inserted into the interior of polymeric tubing 70 through the open proximal end of tubing 70 and extended until rod 74 contacts the interior of tip 12. Rod 74 may be made of metal, ceramic, glass, or a temperature-resistant plastic, and should have a blunt or rounded distal end to avoid puncturing tip 12.

The biaxial orientation of the polymeric tubing is carried out as follows: (1) a predetermined initial length of tubing 70, including the closed seal tip 12, is positioned inside the cavity 58 of the mold and clamped in place with clamp 72; (2) the mold cavity 58 and the portion of tubing 70 in the mold is heated to the appropriate temperature(s)—orientation takes place at a temperature between the first and second order transition temperatures of the polymeric material, preferably between about 77° C.–100° C. for PET tubing; (3) the rod 70 is inserted inside the tubing 70 and extended until it contacts the inside of the tubing tip as shown in FIG. 10A; (4) the tubing 70 is expanded axially by pushing the rod 74 along the longitudinal axis of the tube into the mold so as to axially stretch the tubing 70 to a new length as suggested in FIG. 10A, and shown in FIG. 10B; (5) before, during or after the axial stretching, the tubing is also expanded radially by admitting a fluid under pressure as indicated by arrow 80 in FIG. 10B into the interior of the tubing through a fitting (not shown) to expand the tubing to the interior dimensions of the mold cavity 58 as suggested in FIG. 10B; (6) if desired, the pressure may be adjusted, and at least some portions of the catheter, e.g. the balloon portion, can be subjected to a heat setting step carried out at a temperature above that of the stretching temperature for a time sufficient to increase the degree of crystallinity in the polymeric material; and (7) the tubing is allowed to cool, and the pressure is released from the tubing so that the tubing can be withdrawn from the mold. It should be appreciated that the final shape of the tip 12 is determined by the shape of the mold so that various shapes of tips 12 can be easily provided by modifying the shape of the bottom of cavity 58 to the shape of the desired tip. Alternatively, a special shaping tool can be used to shape or post form the tip 12 after the catheter is removed from the mold. Further, the closed end of the catheter can be provided with a small micro-sized or larger hole by any suitable method, such as cutting or drilling the hole with a laser beam, water stream, or a mechanical drilling or cutting device after the catheter is formed, or forming the hole during the tube sealing step prior to orientation.

Although the above procedure has been described in general terms, the broad parameters of these steps are well-known in the art as described herein. Specific choices of materials, starting and final dimensions, temperatures, times, degree of stretching and expansion, etc. will affect the final size and properties of the single-piece-catheters of this invention. These choices may be varied through routine experimentation in order to optimize particular properties of the resulting catheters. However, for best results, the thickness of the wall of each catheter should be stretched from an initial thickness $T_1$ to a final thickness $T_2$ as a function of the final outer diameter of the catheter $D_2$, stretched from an initial diameter $D_1$, such that the outer diameter to thickness ratio $D_2/T_2$ is within a predetermined range. For catheters of the type shown in FIG. 1, the walls of these catheters, as well as the walls of the proximal and distal body portions of balloon catheters shown in FIGS. 3–6 should have a outer diameter to wall thickness ratio of between 25 and 750. The balloon portions 26 and 36 of the catheters shown in FIGS. 3–6 are of a larger diameter and tend to have a thinner wall so that the preferred ratio is between 150 and 1500. Thus, generally speaking, the outer diameter to wall thickness ratio should be between 25 and 1500. Examples of catheters made in accordance with the above described method are described as follows, wherein density changes have been ignored.

EXAMPLE 1

A cylindrical closed ended tube 70 having an internal diameter of 0.068 inches and outer diameter of 0.081 inches (and thus an initial wall thickness $T_1=0.0065$) is heated and expanded so as to stretch the heated portion of the tube from an initial length $L_1$ to a final length $L_2$ so that $L_2=2.1$ times $L_1$; and the finished catheter (shaped as shown in FIGS. 1 and 2) has a finished inner diameter 0,288 and outer diameter 0.2896, with the resulting wall thickness $T_2=0.0008$ inches. The wall thickness is therefore reduced 8.125 times ($T_2/T_1$). The inner diameter is stretched 4.2 times the initial inner diameter (0.288/0.068) while the outer diameter is stretched 3.6 times the initial outer diameter (0.2896/0.081). The outer diameter to wall thickness ratio $=362$.

EXAMPLE 2

A cylindrical closed end tube 70 having an internal diameter of 0.115 inches and an outer diameter of 0.140 inches (and thus an initial wall thickness $T_1$ of 0.0125 inches) is heated and expanded. The final dimensions of the intermediate section of balloon portion 26 is 0.615 inches outer diameter with a wall thickness of 0.0009 inches. This portion is stretched 2.9 times from its original axial dimension. The proximal and distal portions 28 and 30 each have an outer diameter of 0.288 inches and a wall thickness of 0.0016 inches. These portions of the catheter are axially stretched 3.4 times the original axial dimension. The inner diameter of the balloon portion is stretched 5.3 times its original dimension while the outer diameter is stretched 4.4 times its original dimension. The proximal and distal portions and its inner diameter stretched 2.5 times and its outer diameter stretched 2.1 times. The resulting outer diameter to wall ratio for the balloon is 683, while the ratio of the proximal and distal portions is 180.

The result of these operations is an integral, single-piece, high-strength, inflatable, substantially inelastic thin-walled catheter that is free of seams and joints of any kind. Because a catheter according to this invention has been biaxially oriented along its entire length, including the region surrounding the closed distal tip 12, there are no weak points or discontinuities. The single-piece catheters of this invention can be manufactured faster, less-expensively and with less waste of materials than comparable prior art catheters. No assembly operations are required.

Since certain changes may be made to the above processes and products without departing from the scope of the invention herein involved, it is intended that all matter contained in the above description or shown in the accompanying drawing shall be interpreted in an illustrative and not in a limiting sense.

What is claimed is:

1. A unitary, integral and seamless catheter comprising self supporting tubing having one closed end, said tubing comprising a tubular wall wherein at least a part of said tubular wall defines a balloon portion having a wall thickness on the order of 1.5 mils or less, and another part of said tubular wall defines said closed end portion, both of said portions being integrally formed with said tubular wall, further wherein said tubing consists essentially of an orientable polymeric material which has been biaxially oriented along substantially the entire length of said tubular wall and said closed end portion, said catheter having an overall longitudinal dimension at least double the longitudinal dimension of said balloon wall portion and also being sufficiently thin-walled so that said tubing is flexible, inflatable and collapsible.

2. The catheter of claim 1, wherein said tubing includes a body portion and a balloon portion.

3. Catheter according to claim 2 further wherein said body portion has a longitudinal dimension substantially greater than the outside diameter of said tubing.

4. Catheter according to claim 3 wherein said longitudinal dimension of said body portion is at least four times the outside diameter of said tubing.

5. The catheter of claim 2, wherein the tubing is dimensioned so that the outer diameter to wall thickness ratio of said body portion is between 25 and 750, and outer diameter to wall thickness ratio of said balloon portion is between 150 and 1500.

6. The catheter of claim 1, wherein said polymeric tubing consists essentially of polyethylene terephthalate.

7. The catheter of claim 1, wherein said tubing is heat set after being biaxially formed.

8. The catheter of claim 1, wherein the tubing is dimensioned so that the outer diameter to wall thickness ratio of at least a portion of said tubing is between 25 and 1500.

9. The catheter of claim 1, wherein said closed end is rounded.

10. The catheter of claim 1, wherein said closed end is tapered toward the longitudinal axis of said tubing.

11. The catheter of claim 1, wherein said closed end is curved about the longitudinal axis of said tubing.

12. The catheter of claim 1, wherein the radial tensile strength of said material is about 10,000 psi or greater.

13. A unitary, integral and seamless balloon catheter consisting essentially of an orientable polymeric tubing comprising a balloon portion and proximal and distal body portions at the respective ends of said balloon portion, said distal body portion terminating at a closed end curved about the longitudinal axis of said tubing in a direction concave with respect to said balloon portion, further wherein said catheter has been biaxially oriented along its entire length and distal end and has an overall longitudinal dimension at least double the longitudinal dimension of said balloon portion.

14. Catheter according to claim 13 wherein the sum of the longitudinal dimensions of said proximal and distal body portions is equal to or greater than the longitudinal dimension of said balloon portion.

15. Catheter according to claim 14 further wherein said catheter has an overall longitudinal dimension substantially greater than the outside diameter of said tubing.

16. The catheter of claim 13, wherein said polymeric tubing consists essentially of polyethylene terephthalate.

17. Balloon dilatation catheter apparatus comprising:
   (a) elongated, flexible, thin-walled, substantially inelastic polymeric tubing having an open proximal end, a biaxially oriented closed distal end, and an interior passageway having a substantially constant tubing diameter when said apparatus is inflated, said passageway being defined by biaxially-oriented tubing wall means;
   (b) a very thin-walled, flexible, high strength, substantially inelastic polymeric balloon which is readily inflatable under fluid pressure and readily collapsible under vacuum, said balloon being located between the proximal and distal ends of said tubing, said balloon comprising an interior having a substantially constant balloon diameter that is substantially independent of the fluid inflation pressure when said apparatus is inflated, said balloon diameter being greater than said tubing diameter, and said balloon being defined by biaxially-oriented balloon wall means having a thickness of about 1.5 mils or less; and
   (c) integrally formed biaxially-oriented wall means joining said tubing wall means to said balloon wall means in a unitary, integral and seamless construction, further wherein said catheter apparatus has an overall longitudinal dimension at least double the longitudinal dimension of said balloon.

18. Catheter apparatus according to claim 17 wherein the apparatus has an overall longitudinal dimension substantially greater than the outside diameter of said tubing.

19. Catheter apparatus according to claim 18 wherein said longitudinal dimension of the apparatus is at least four times the outside diameter of said tubing.

20. Catheter apparatus according to claim 18 wherein said longitudinal dimension of the apparatus is about two thousand times the outside diameter of said tubing.

21. Balloon dilatation catheter apparatus according to claim 17 further wherein the ratio of said tubing diameter to the thickness of said tubing wall means is between 25 and 750.

22. Balloon dilatation catheter apparatus according to claim 17 further wherein the ratio of said balloon diameter to the thickness of said balloon wall means is between 150 and 1500.

23. Balloon dilatation catheter apparatus according to claim 17 further wherein the ratio of said tubing diameter to the thickness of said tubing wall means is between 25 and 750, and the ratio of said balloon diameter to the thickness of said balloon wall means is between 150 and 1500.

24. Balloon dilatation catheter apparatus according to claim 17 wherein said tubing and said balloon consist essentially of polyethylene terephthalate.

25. Balloon dilatation catheter apparatus according to claim 17 wherein said tubing and said balloon have been heat set after being biaxially oriented.

26. A high-strength, thin-walled catheter made by the process of:

(a) heating a thin-walled tubular element having a tubular wall, a sealed distal end integrally formed with the tubular wall and an open proximal end and consisting essentially of orientable polymer to a temperature between the first and second order polymer transition temperatures;
(b) axially orienting the entire heated tubular element including the sealed distal end;
(c) radially orienting the entire heated tubular element including the sealed distal end by introducing a pressurized fluid into said tubing through the open proximal end thereof;

such that the steps (b) and (c) of orienting the tubular element stretches the element so that at least a portion of the stretched tubular element forms a balloon portion having a wall thickness less than or equal to 1.5 mils, the outer diameter to wall thickness ratio of said balloon portion is between 25 and 1500, the sealed distal end is biaxially oriented and said catheter has an overall longitudinal dimension at least double the longitudinal dimension of said balloon portion.

27. The catheter of claim 26, wherein said steps (b) and (c) include the steps of orienting the tubular element so as to form at least one body portion and a balloon portion, wherein the outer diameter to wall thickness ratio of said body portion is between 25 and 750 and said balloon portion is between 150 and 1500.

28. Catheter according to claim 26 wherein said orientable polymer consists essentially of polyethylene terephthalate.

* * * * *

UNITED STATES PATENT AND TRADEMARK OFFICE
CERTIFICATE OF CORRECTION

PATENT NO. : 5,411,477
DATED : May 2, 1995
INVENTOR(S) : Mark A. Saab

It is certified that error appears in the above-indentified patent and that said Letters Patent is hereby corrected as shown below:

Col. 11, line 41 - delete "robing" and substitute therefor -- tubing --.

Signed and Sealed this

Fifteenth Day of August, 1995

Attest:

BRUCE LEHMAN

Attesting Officer    Commissioner of Patents and Trademarks